United States Patent [19]
Kopfer

[11] Patent Number: 5,191,364
[45] Date of Patent: Mar. 2, 1993

[54] PROTECTIVE EYEWEAR FOR USE IN SPORTS AND THE LIKE

[76] Inventor: Rudolph J. Kopfer, P.O. Box 2894, Ketcham, Id. 83340

[21] Appl. No.: 601,467

[22] Filed: Oct. 23, 1990

Related U.S. Application Data

[63] Continuation-in-part of Ser. No. 405,421, Sep. 11, 1989, abandoned.

[51] Int. Cl.⁵ ............................................. G02C 5/08
[52] U.S. Cl. .................................... 351/62; 351/43; 2/436
[58] Field of Search ............ 351/41, 63, 118, 62, 351/159, 43, 115; 2/436, 446, 452, 437, 43, 439; 359/795

[56] References Cited

U.S. PATENT DOCUMENTS

| | | | |
|---|---|---|---|
| Re. 12,924 | 3/1909 | Cover . | |
| D. 293,504 | 1/1988 | Specht | D16/107 |
| D. 295,533 | 5/1988 | Wichers | D16/102 |
| 1,031,859 | 7/1912 | Malcom | 2/439 |
| 1,168,581 | 1/1916 | Troppman . | |
| 1,433,676 | 10/1922 | Cover . | |
| 1,478,818 | 12/1923 | Cover . | |
| 1,562,350 | 11/1925 | Luckey . | |
| 1,669,229 | 5/1928 | Cook . | |
| 1,677,747 | 7/1928 | Cook . | |
| 1,720,814 | 7/1929 | Baker . | |
| 1,741,427 | 12/1929 | Meyrowitz . | |
| 1,754,694 | 4/1930 | Neuwirth . | |
| 1,846,679 | 2/1932 | Fischer . | |
| 1,853,872 | 4/1932 | Meyrowitz . | |
| 1,936,746 | 11/1933 | Baker . | |
| 1,989,876 | 2/1935 | Meyrowitz . | |
| 2,002,543 | 5/1935 | Meyrowitz . | |
| 2,007,186 | 7/1935 | Farrell | 2/14 |
| 2,026,435 | 12/1935 | Ratti | 2/14 |
| 2,088,262 | 7/1937 | Grano . | |
| 2,182,104 | 12/1939 | Wilen | 2/14 |
| 2,321,159 | 6/1943 | Ryan | 88/41 |
| 2,364,584 | 12/1944 | Malcolm | 2/14 |
| 2,387,821 | 10/1945 | Baratelli et al. . | |
| 2,446,048 | 7/1948 | Kimball . | |
| 2,526,181 | 10/1950 | Wilen | 2/14 |
| 2,608,687 | 9/1952 | Ellis | 2/14 |
| 2,846,684 | 8/1958 | Hill | 2/14 |
| 2,865,253 | 12/1958 | Thielens . | |
| 3,040,616 | 6/1962 | Simpson . | |
| 3,419,909 | 1/1969 | Spain . | |
| 3,556,644 | 1/1971 | Stahl | 351/118 |
| 3,865,619 | 2/1975 | Pennewiss | 117/138.8 |
| 4,099,858 | 7/1978 | Land | 351/62 |
| 4,264,987 | 5/1981 | Runckel | 2/428 |
| 4,405,212 | 9/1983 | Cooper | 351/43 |
| 4,468,819 | 9/1984 | Ohno . | |
| 4,544,245 | 10/1985 | Stansbury | 351/118 |
| 4,547,049 | 10/1985 | Cotie . | |
| 4,654,899 | 4/1987 | Harris | 2/436 |
| 4,707,863 | 11/1987 | McNeal | 2/436 |
| 4,717,249 | 1/1988 | Fischer | 351/43 |
| 4,741,611 | 5/1988 | Burns | 351/44 |
| 4,785,481 | 11/1988 | Palmer, III et al. . | |
| 4,792,221 | 12/1988 | Parks | 351/118 |
| 4,867,553 | 9/1989 | Frieder . | |
| 4,877,320 | 10/1989 | Holden . | |
| 4,955,708 | 9/1990 | Kahaney | 351/118 |

FOREIGN PATENT DOCUMENTS 56-133716 10/1981 Japan .

Primary Examiner—Rodney B. Bovernick
Attorney, Agent, or Firm—Haverstock, Medlen & Carroll

[57] ABSTRACT

Protective eyewear for sports activities and the like having a resilient rigid frame is disclosed. Included is a sealing area around the eyes having a web which diverges outwardly in every direction toward the lens frame. The frame is curvedly contoured around the face of the user and in conjunction with the diverging web, provides both maximum eye protection and peripheral visibility. A semi-rigid frame provides for temple mounting and obviates the need for around-the-head straps.

25 Claims, 5 Drawing Sheets

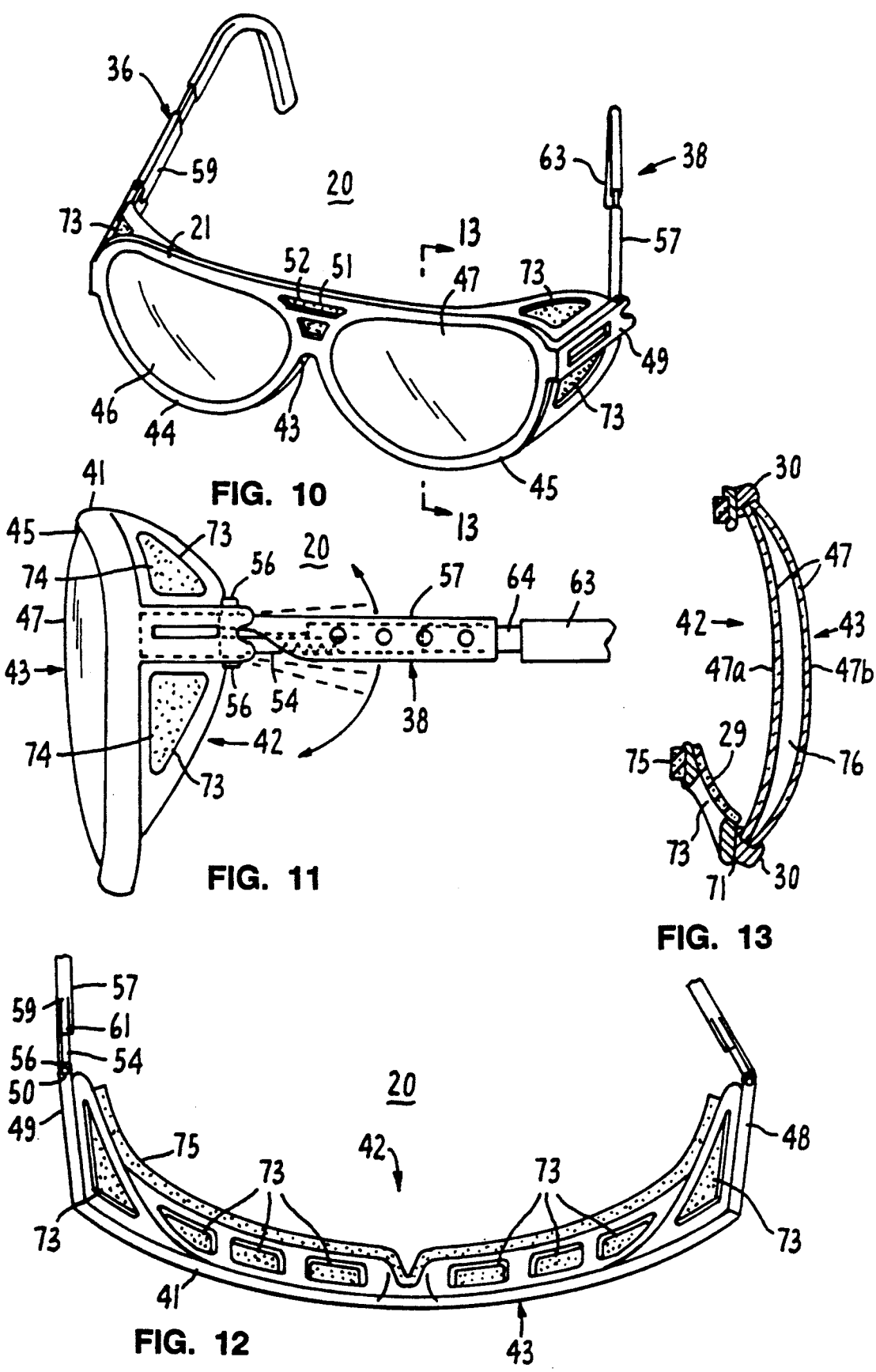

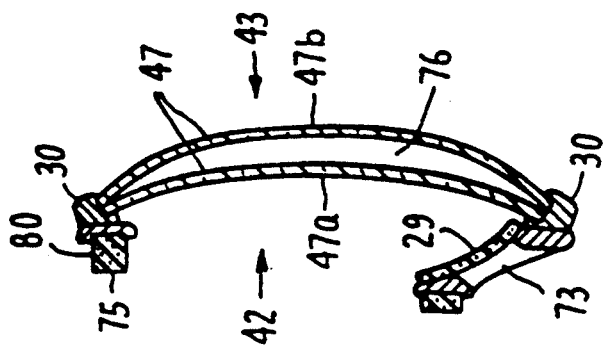
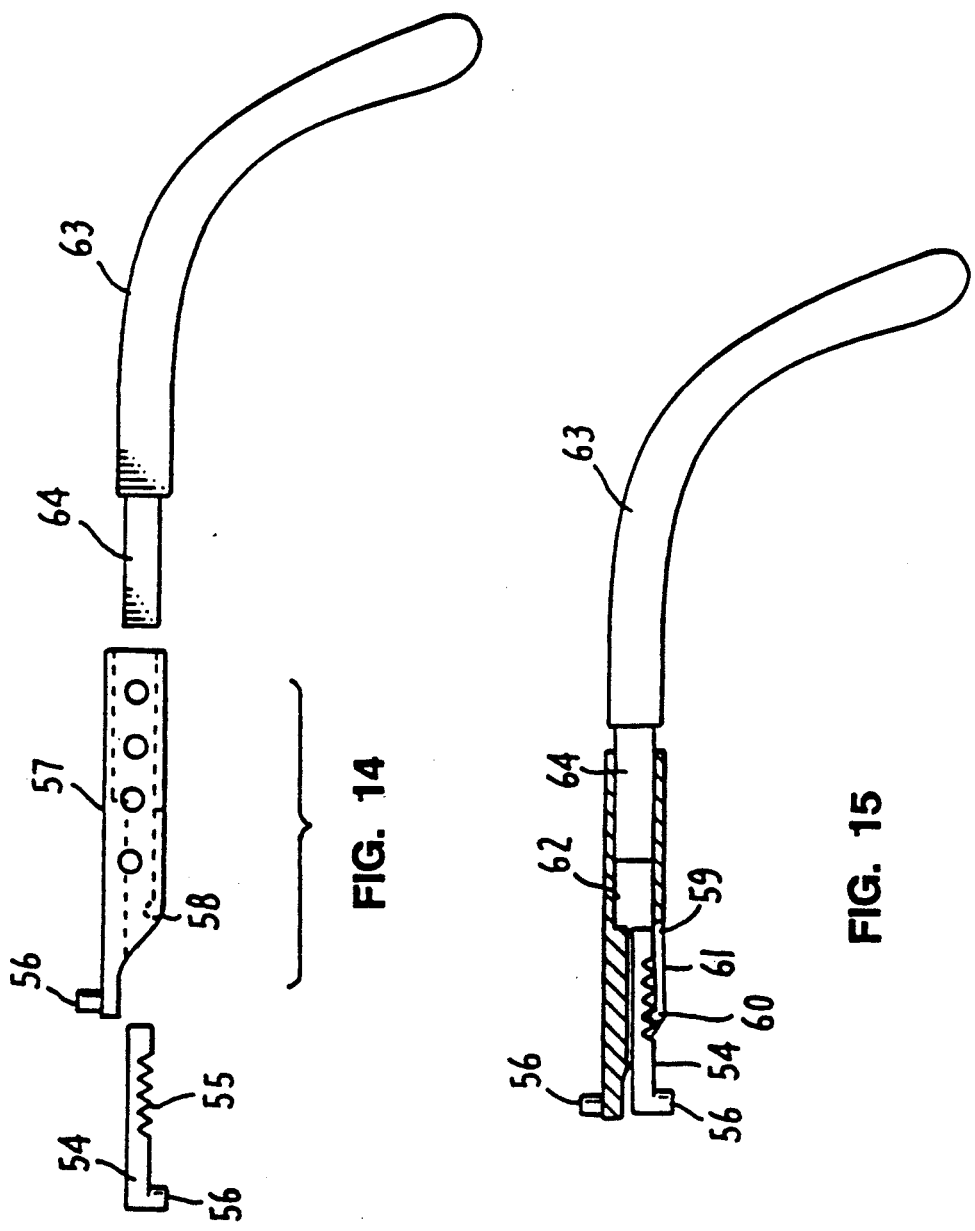

5,191,364

PROTECTIVE EYEWEAR FOR USE IN SPORTS AND THE LIKE

TECHNICAL FIELD OF THE INVENTION

This application is a continuation-in-part of application Ser. No. 405,421 filed Sep. 11, 1989 now since abandoned.

This invention relates to protective eyewear for use in sports and the like. The eyeglasses are configured in a wrap around design. The eye support is contoured to snugly fit the eye orbital and diverge therefrom outward to the lens support area of the frame to provide for maximum peripheral vision of at least 140 degrees.

BACKGROUND OF THE INVENTION

This invention relates to protective eyewear for use in sports and the like. The device which is the subject of this application is adapted to provide the prophylactic eye protection of goggles while giving the appearance of light weight, streamlined eye glasses with an unobstructed field of vision.

Many diverse types of sports and other activities of necessity suggest that the participant wear some type of eye protection. Consequently, there are different types of eyeglasses and goggles which are appropriate for each activity. For example, in bad weather snow skiers want eye protection that prevents the penetration of wind, rain, snow, sleet, sand, dirt, dust and peripheral glare into the eyes. In fair weather, the desire for eye protection may be limited to protection against sun glare.

For snow skiing, in the prior art, sunglasses sufficed as eye protection from the sun. Sunglasses were light weight, compact, stylish, easily put on and taken off, and did not obstruct the wearer's field of vision. Sunglasses were attached along the temples, around the ears, and not around the back of the head. Such attachment necessarily required that the frame be at least semi-rigid.

In the prior art protective eyewear goggles were necessary for bad weather. Goggles, however, are large, cumbersome, awkward and difficult to wear. Most skiers, and other sports participants, find this objectionable. Preferable is the unrestraining fit and convenience offered by eye glasses which are lightly retained on the face of the user.

Prior art devices such as those disclosed in U.S. Pat. No. 1,669,229 Cook, U.S. Pat. No. 1,677,747, U.S. Pat. No. 1,936,746 Baker, and U.S. Pat. No. 1,754,694 Neuwirth unsuccessfully attempted to modify eyeglasses to provide all weather goggle-like eye protection while retaining the appearance and advantages of eyeglasses. These prior art devices were fitted with rubber, foam or some other non-rigid substance around the inside perimeter of the eyeglasses in an attempt to form an acceptable seal. However, as the non-rigid material easily deformed, it would not necessarily retain its resiliency and its shape after multiple uses, and would thereby become ineffective after a short period of time. Further, the placement of the non-rigid substance blocked peripheral vision, thereby severely restricting the wearer's field of vision.

Moreover, unlike eyeglasses, goggles are customarily held in place by an elastic or adjustable head band. Goggles use a strap around the wearer's head, as the frame is flexible; goggles do not support temple bars because of their non-rigid frame.

For goggles to create a protective seal, the head band is positioned circumferentially around the back of the wearer's head. The head band is attached, at both ends, to the goggle mask which is bent around the wearer's face. In this manner, goggles provide a larger field of vision and a tight seal against the user's face thereby shielding the user's eyes from the elements.

Although goggles form a shielding seal around the face, goggles are not a preferred form of eyewear; goggles are typically large, non-rigid, bulky, awkward, and uncomfortable to the wearer. These problems are substantially obviated by the present invention, which provides a spectacle like frame with all of the protective benefits of goggles, while not impinging on the wearer's field of vision.

SUMMARY OF THE INVENTION

The present invention overcomes all of the inherent deficiencies and limitations in the prior art devices. The present invention is light weight, aesthetically pleasing, comfortable, and can be used to protect the eyes in any type of weather. It gives the appearance of eyeglasses while offering substantially more eye protection, without diminution in the wearer's field of vision.

The present invention provides a resilient semi-rigid or rigid frame having a sealing area around the eyes with a web which diverges outwardly toward the frame. The frame is curvedly contoured around the face of the user and in conjunction with the diverging web, provides maximum peripheral visibility.

The diverging web of the frame, and/or the inside of the frame, may be provided with a plurality of vent holes to promote the circulation of air and thereby inhibit misting of the inner surface of the lenses. Advantageously, a ram air intake can be provided in the front face of the frame and disposed in the nose bridge area. However, the ram air intake can be located elsewhere on the front of the frame, if desired. The various vent holes and air intakes may also be covered with a thin breathable cellular foam material to further shield the user from the elements.

Accordingly, a lens, or pair of lenses, is secured at the frame. The lens, or pair of lenses, may be of a double-walled construction. Each double-walled construction, having two lenses, may be either separated by an air space or abutted against one another. If an air space is provided, the two lenses may have a different base curve to provide an air space while having a common peripheral edge, or they may have the same radius of curvature with a peripheral seal or gasket between them.

Preferably, the lenses are a new style of double lens in which the forward lens is convex and the rear lens is concave (the words "convex" and "concave" are used here meaning curved in both the horizontal and vertical directions), and the two lenses are bonded together along a single peripheral edge. These lenses may be formed with zero power in which the forward and rearward lenses are each constant thickness and different spherical radii of curvature to permit their edges to converge for bonding. Alternatively, a prescription may be ground into either lens. Special coatings can be provided on the adjacent faces of the two lenses which are protected from oxidation or scratching.

The present invention may be further provided with a cushion around the sealing area for increased sealing and protection.

Fixed positioning of the sports eyeglasses is accomplished by temple bars. The angular disposition of the general plane in which the frame lies may be further adjusted by providing adjusting connections at the temples. Each connection can be accomplished by a pivotal rack and pawl connection between the temple bars and the frame.

The frame includes a pair of temple bar stubs being attached to the frame at opposing ends. In one embodiment, a pair of temple bars are pivotally attached to each temple bar stub using a unique pivot pin and hole engagement configuration. Each temple bar includes a receiving segment having a pivot pin, rack receiving recess and an earpiece receiving channel. Thus, in this embodiment, the angle of the frame, with respect to the user's face, is dependant upon which particular tooth of the rack segment engages the pawl members.

The temple bars may also be provided with length adjustable earpieces and mastoid hooks to further aid in fitting the sports eyeglasses to the head and face of the user.

This invention is to provides protective eyewear for use in any type of weather.

Objects of the invention will become apparent upon reading the following specification and referring to the accompanying drawings.

BRIEF DESCRIPTION OF THE DRAWINGS

FIG. 10 is a front elevation view of another embodiment of sports eyeglasses.

FIG. 11 is a left side view of the temple bar and frame orbital adjusting connection.

FIG. 12 is a bottom view of the frame and frame orbital adjusting connection.

FIG. 13 is a cross section taken along section line 13—13 of FIG. 10.

FIG. 14 is an exploded side view of the left temple bar.

FIG. 15 is partial cutaway assembled view of FIG. 14.

FIG. 16 is an analogous view to that of FIG. 13 showing another embodiment of the sports eyeglasses having perspiration channel in the upper portion of the orbital sealing gasket.

DESCRIPTION OF THE PREFERRED EMBODIMENTS

Figure 1:
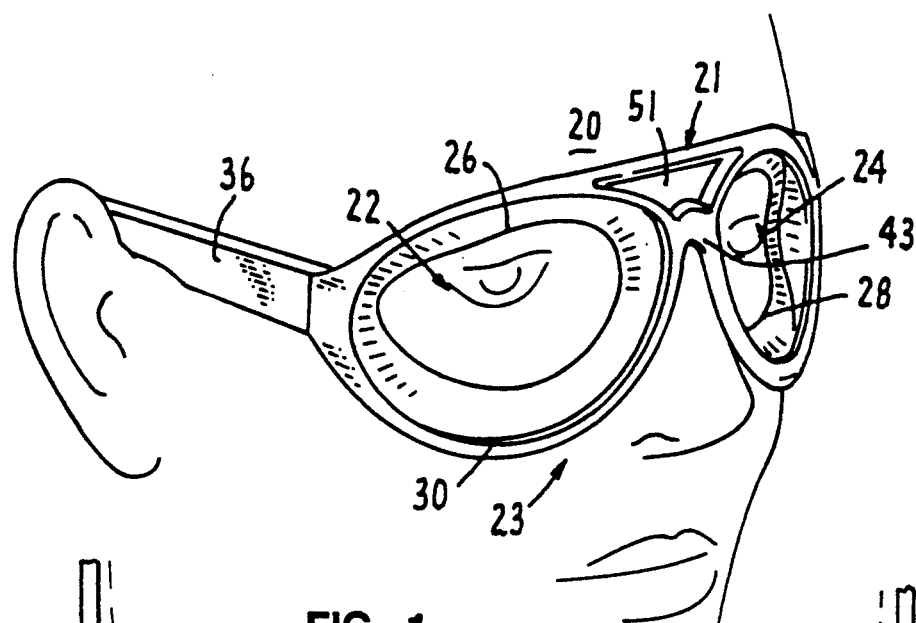
FIG. 1 is a front elevation view of sports eyeglasses shown worn by a user.
Figure 3:
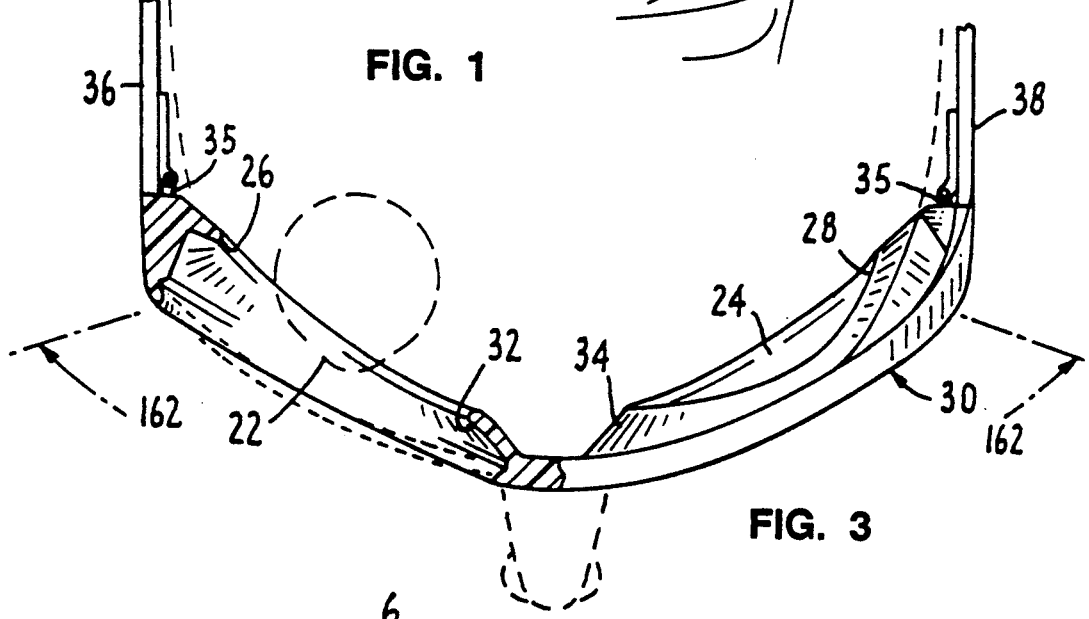
FIG. 3 is a cross section of FIG. 2 showing one embodiment of attachment of temple bar for sports eyeglasses.
Figure 2:
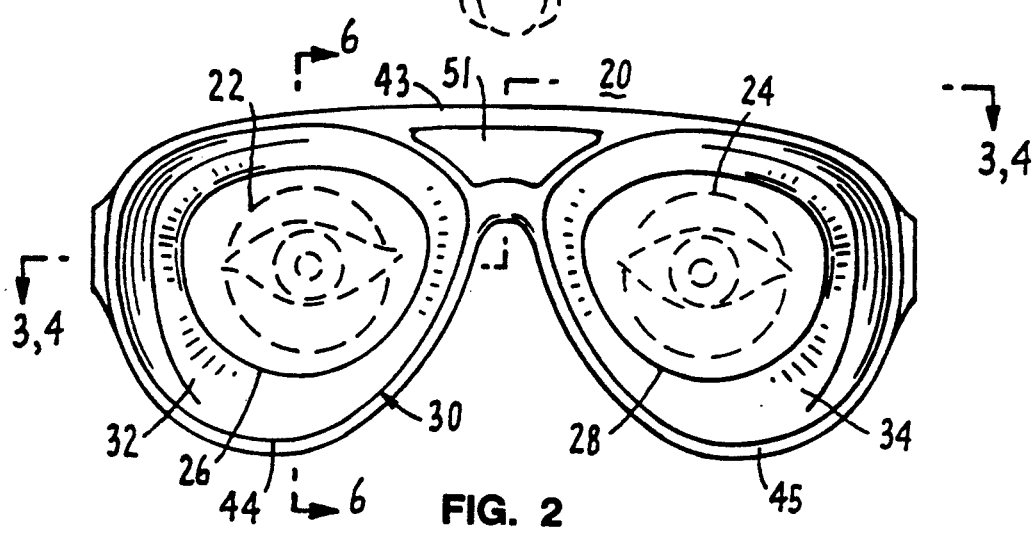
FIG. 2 is a front view of the sports eyeglasses of the present invention.
Figure 4:
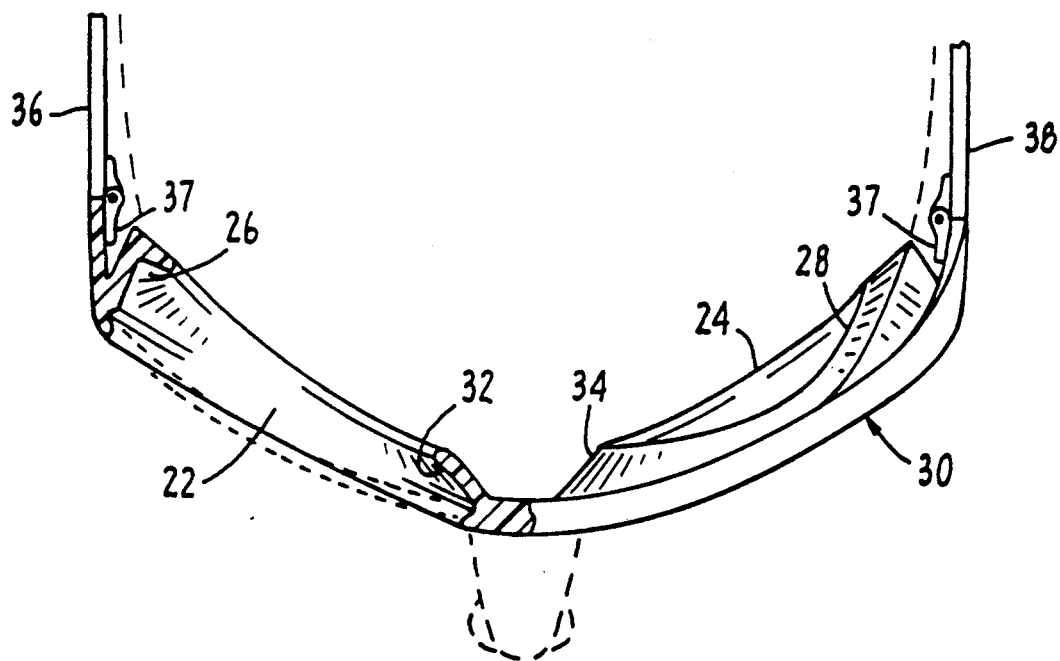
FIG. 4 is a cross section of FIG. 2 showing another embodiment of attachment of temple bar for sports eyeglasses.
Figure 5:
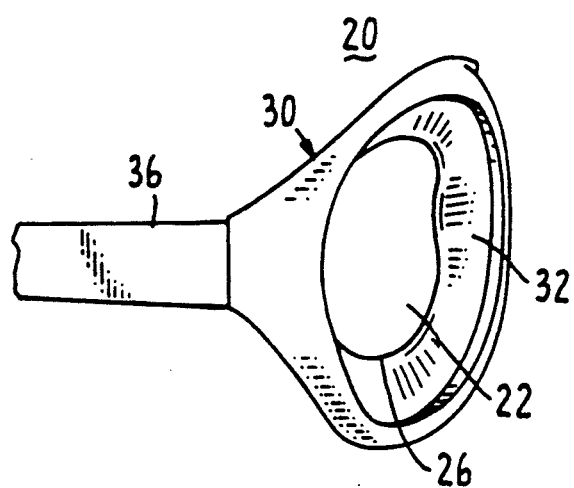
FIG. 5 is a partial side view of the right side of sports eyeglasses.

Referring now to FIGS. 1-16, sports eyeglasses 20 are shown. Generally, sports eyeglasses 20 have a frame 21 which is attached to temple bars 36 and 38. Temple bars 36 and 38 are adapted to support the frame 21 on the wearer's head. In one embodiment, shown in FIG. 3, the temple bars 36 and 38 are attached to the frame 21 with 90 degree angle hinge 35. In FIG. 4, another embodiment, the frame 21 is extended to accommodate attachment of the temple bars and 38 with 180 degree angle hinge 37. Temple bars 36 and 38 may further be provided with mastoid hooks (not shown) which enhance the securing capability of the temple bars 36 and 38.

Figure 6:
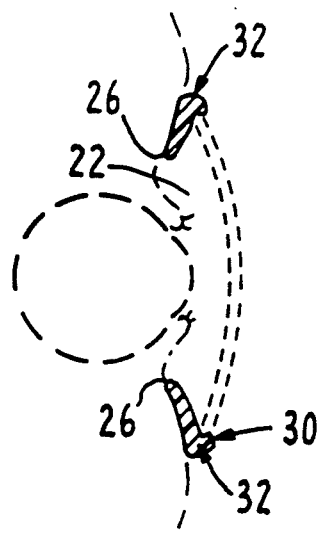
FIG. 6 is a cross section of the web taken along section 6—6 of FIG. 2, showing the position of the eye when worn by the wearer.
Figure 7:
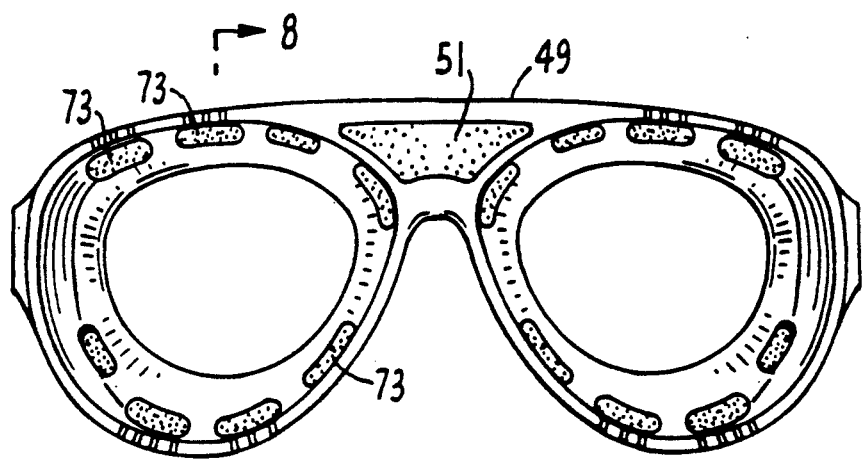
FIG. 7 is a front view of sports eyeglasses, having orbital sealing gaskets, with the lenses removed.
Figure 8:
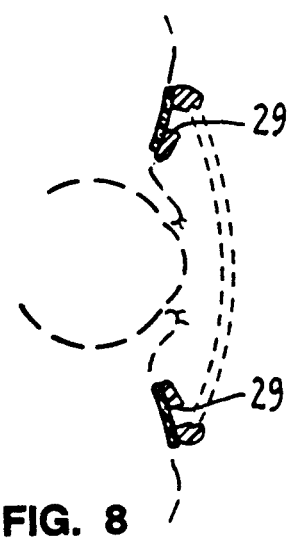
FIG. 8 is a cross section of the web taken along section 8—8 of FIG. 7, showing the position of the eye when worn by the wearer.

The frame 21 is contoured in a wrap around configuration and has right lens opening 44 and left lens opening 45 in the lens support area 30. As shown in FIGS. 1-16, the frame 21 has a pair of eye apertures 22 and 24 which are adapted to be aligned with the wearer's eyes. Lens support area 30 surrounds the eye apertures 22 and 24. Each eye aperture 22 and 24 is provided with a sealing area 26 and 28, respectively, which surrounds the eye aperture 22 or 24, and which snugly fits against the skin of the wearer adjacent to the eye. Referring to FIGS. 3, 6 and 8, it is shown that the eye itself is forward of the sealing area 26 or 28 when the sports eyeglasses 20 are properly positioned on the face 23 of the wearer.

Webs 32 and 34 diverge from each sealing area 26 and 28, respectively to the lens support area 30 for enclosure of each eye without obstructing peripheral vision. Webs 32 and 34 attach to the interior side 42 of frame 21 at its divergent side. As shown in FIG. 3, the wearer is able to see at least 140 degrees and preferably over 160 degrees of peripheral vision with both eyes as indicated by the peripheral vision angle 162 in FIG. 4. The webs 32 and 34 may be provided with vent holes 73 to promote air circulation. The vent holes may be continuous with air grooves situated on the inner aspect of the lens support area but not evident from the front view. Vent holes 73 may be covered with cellular foam material 29 to further shield the user.

It can be seen that sports eyeglasses 20 are contoured to wrap around and closely fit the orbital area of the user which is the area barred by the user's nose, eyebrow and cheek bone. The exterior side 43 of sports eyeglasses 20 has a generally standard singles appearance, while the interior side 42, shown, for example, in FIG. 12, has more of a goggle-type appearance.

Figure 9:
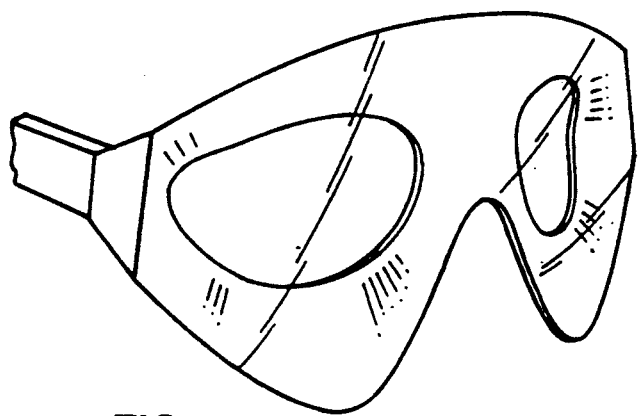
FIG. 9 is a front elevation view of another embodiment of sports eyeglasses having a single lens.

The lens support area 30 supports at least one lens. Typically, two lenses 46 and 47 are housed by the lens support area 30 in the frame 21. However, as shown in FIG. 9, a continuous lens which covers both right lens opening 44 and left lens opening 45 may be used. The lenses may be of single or double-walled construction, as illustrated in FIG. 13. In a double-walled construction, the lenses may have an airspace 76 and different radii of curvature. The double walled lenses may also have a single peripheral edge.

Between right lens opening 44 and left lens opening 45 there is positioned a ram air intake 51 for directing filtered air into the eye chamber through the vent holes. Referring to FIG. 10, ram air intake 51 may be covered with ram air intake filter cover 52. Construction of ram air intake filter cover 52 typically can be from a thin breathable cellular foam material.

Alternatively, ram air intake 51 can be circumferentially covered on the inner side so that the ram air intake 51 appears to be open when viewed from the exterior side 43 of the sports eyeglasses 20. With the circumferential covering of ram air intake 51, intake air passing through is directed venturily down through those the vents 73 enclosed by the circumferential covering in the webs 32 and 34 to enhance ventilation and decrease the formation of mist on the lenses 46 and 47 of the sports eyeglasses 20.

FIGS. 10-16 show a further embodiment of the present invention. In the embodiment depicted in FIGS. 10-16, a pair of the temple bars 36 and 38 meet temple bar stubs, right temple bar stub 48 and left temple bar stub 49, which are attached and extend outward from opposite ends of the frame 21. Both temple bar stubs 48 and 49 have upper and lower pivot pin engagement holes 50 for engaging the temple bars 36 and 38. For the sake of illustration, only the left temple bar 38 is shown in its entirety. However, it should be apparent that right temple bar 36 is identical in construction and is a mirror image of left temple bar stem 53. Left temple bar 38 has left rack arm 54 pivotally attached to left temple bar stub 49 via pivot pin 56 and lower pivot pin engagement hole 50. The left rack segment 55 of left rack arm 54 is slidably received within left rack arm receiving recess 58 in left receiving segment 57. Left receiving segment 57 is also provided with a pivot pin 56 which pivotally engages the upper pivot pin engagement hole 50 in left temple bar stub 49.

Left pawl arm 59 is attached within left rack arm receiving recess 58 and generally has a left resilient pawl member 61 attached at one end and includes a left pawl or protuberance 60 at its other end for engaging left rack segment 55. Advantageously, the opening in left rack arm receiving recess 58 is sized to closely receive left rack arm 55. Left resilient pawl member 61 bends downwardly to allow the adjustable movement. The angle which frame 21 makes with respect to right and left temple bar 36 and 38, is dependent upon which particular tooth of rack segment 55 with which pawls 60 are engaged.

The back portion of left receiving segment 57 is also provided with left earpiece receiving channel 62 with slidably and frictionally engages channel member 64. Channel member 64 is colinearly attached to left earpiece 63, thereby providing a length adjustable earpiece 63 for sports eyeglasses 20.

Again, a right orbital adjusting connection is similarly constructed to the left orbital adjusting connection previously explained, and is shown best in FIG. 12.

FIG. 16 shows a second embodiment of sports eyeglasses 20 which includes a perspiration channel 80 in the upper portion of orbital sealing gasket 75. Orbital sealing gasket 75 may be added to sealing area 26 and 28 to enhance the seal and/or provide a facial cushion. Advantageously, the upper portion of orbital sealing gasket 75 is manufactured of a non-porous foam cushion material so as not to absorb perspiration. The orbital sealing gasket 75 could be manufactured from any suitable material and/or in a compressible accordion fashion to provide a tight seal against the face of the user.

Perspiration channel 80 runs along the top of the of the frame 21 such that perspiration from the forehead of the user is directed to the lateral sides of sports eyeglasses 20, away from the face and eyes of the user.

Other modifications include addition of a nosepiece, enlarging the upper and/or lower portions of the lens frame and corresponding lenses to enhance superior and inferior vision. This is especially desirable in a sport such as bicycling where the user head is oftentimes face down, forcing the user to look out the top portion of the lens.

Additionally, to frame 21 there may be added apertures to provide for increased venting through the interior of the sports eyeglasses 20. A further modification can include the insertion of grooves and/or a metal rod 49 at the interior of the frame 2 across the nose of the wearer for flexibility and fit.

While there is shown and described the present preferred embodiment of the invention, it is to be distinctly understood that this invention is not limited thereto but may be variously embodied to practice within the scope of the following claims.

I claim:

1. A protective eyewear device for use in sports and the like comprising:
   a semi-rigid frame having
      a pair of eye apertures adapted to be aligned with a wearer's eyes,
      a sealing area surrounding each aperture adapted to engage the wearer's skin adjacent to the eye,
      a lens support area surrounding each aperture with the sealing areas and lens support areas positioned to permit at least about 140 degrees peripheral vision with both eyes,
      a web diverging from each sealing area to the adjacent lens support area in every direction to enclose the eye without obstructing the peripheral vision, said web including ventilating apertures covered with permeable foam for substantially preventing the passage of wind and foreign material therethrough, said web further having a foam means contoured to partially cover the web so that air is trapped and directed through the ventilation apertures to increase air circulation;
   curved lens means covering the apertures in the frame at the lens support areas; and,
   a pair of temple bar means attached to the frame and adapted to support the frame on the wearer's head.

2. The eyewear of claim 1 wherein said frame is rigid.

3. The eyewear of claim 1 additionally comprising air grooves on the inner aspect of the lens support area of said frame continuous with the ventilating apertures.

4. The eyewear of claim 1 in which said frame additionally includes a nosepiece, said nosepiece having a pair of nosepads adapted to conformedly contact the nose of the wearer.

5. The eyewear of claim 1 additionally comprising a support means horizontally positioned at the top of the frame bridging the region from one lens support area to the other lens support area.

6. The eyewear of claim 1 additionally comprising a foam means behind the lens support means and substantially covered by the lens support means when viewed from the front of the wearer.

7. The eyewear of claim 1 additionally including a sealing gasket on each sealing area.

8. The eyewear of claim 7 wherein said sealing gasket includes a perspiration channel disposed along its upper portion for directing perspiration away from the eyes and face of the wearer.

9. The eyewear of claim 1 wherein said temple bar means supports the frame on the wearer's head by extending towards and wrapping around a wearer's ears.

10. The eyewear of claim 1 wherein said temple bar means supports the frame on the wearer's head by extending toward and conformedly hugging the wearer's skull region behind the wearer's ears.

11. The eyewear of claim 1 additionally comprising an orbital adjusting means operably connected between said temple bar means and said frame for adjusting the angle of said frame with respect to said temple bar means.

12. The eyewear of claim 11 additionally comprising:
a pair of receiving segments each being pivotally attached at an opposing end of said frame, each said receiving segment having a rack receiving recess and an earpiece receiving channel;
a pair of rack arms, each said rack arm being pivotally attached to an end of said frame and received by one of said rack receiving recesses in one of said receiving segments, each said rack arm having a rack segment including a plurality of teeth; and,
a pair of pawl arms, each being attached within one of said pair of rack receiving recesses and being disposed to frictionally engage the teeth of said rack segments to angularly predispose said frame with respect to said temple bars.

13. A protective eyewear device for use in sports and the like comprising:
a semi-rigid frame having
a pair of eye apertures adapted to be aligned with a wearer's eyes,
a sealing area surrounding each aperture adapted to engage the wearer's skin adjacent to the eye, said sealing area including a sealing gasket with a perspiration channel disposed along its upper portion for directing perspiration away from the eyes and face of the wearer,
a lens support area surrounding each aperture with the sealing areas and lens support areas positioned to permit at least about 140 degrees peripheral vision with both eyes, and,
a web diverging from each sealing area to the adjacent lens support area in every direction to enclose the eye without obstructing the peripheral vision, and including ventilating apertures therethrough;
curved lens means covering the apertures in the lens support areas; and,
a pair of temple bar means attached to the frame and adapted to support the frame on the wearer's head.

14. The eyewear of claim 13 in which said ventilating apertures are covered by permeable foam for substantially reducing the passage of wind and foreign material through the ventilating apertures.

15. The eyewear of claim 13 in which the frame is substantially rigid.

16. The eyewear of claim 13 additionally comprising air grooves on the inner aspect of the lens support area of said frame continuous with the ventilating apertures.

17. The eyewear of claim 13 in which said frame additionally includes a nosepiece, said nosepiece having a pair of nose pads adapted to conformedly contact the nose of the wearer.

18. The eyewear of claim 13 additionally comprising a support means horizontally positioned at the top of the frame bridging the region from one lens support area to the other lens support area.

19. The eyewear of claim 13 wherein said temple bar means supports the frame on the wearer's head by extending towards and wrapping around a wearer's ears.

20. The eyewear of claim 13 wherein said temple bar means supports the frame on the wearer's head by extending toward and conformedly hugging the wearer's skull region behind the wearer's ears.

21. A lens frame for use with lenses in an eyewear device for use in sports and the like, said lens frame comprising:
a pair of eye apertures adapted to be aligned with a wearer's eyes;
a sealing surface surrounding each aperture, said sealing surface adapted to engage the wearer's skin adjacent to the wearer's eyes;
a lens support surface surrounding each aperture, with the sealing surfaces and the adjacent lens support surfaces positioned to permit at least about 140 degrees peripheral vision with both eyes;
a web extending from each sealing surface to the adjacent lens support surface to enclose the eye without substantially obstructing the user's peripheral vision, said web including ventilating apertures covered with permeable foam for substantially reducing the passage of wind and foriegn material therethrough, said web further having a foam means contoured to at least partially cover the web so that air is trapped and directed through the ventilation apertures to increase air circulation when a lens covers said lens support surface.

22. The lens frame of claim 21 additionally comprising air grooves on the lens support surface continuous with the ventilating apertures.

23. The lens frame of claim 21 additionally comprising a foam means behind the lens support surface and at least partially covered by the lens support surface when viewed from the front of the wearer.

24. The lens frame of claim 21 additionally comprising a sealing gasket on each sealing surface.

25. The lens frame of claim 24 wherein said sealing gasket has a perspiration diversion means along an upper portion for directing perspiration away from the eyes and face of the wearer.

* * * * *

UNITED STATES PATENT AND TRADEMARK OFFICE
CERTIFICATE OF CORRECTION

PATENT NO. : 5,191,364

DATED : March 2, 1993

INVENTOR(S) : RUDOLPH J. KOPFER

It is certified that error appears in the above-identified patent and that said Letters Patent is hereby corrected as shown below:

In column 4, Line 14, after "bars" insert --36--.

In column 6, Line 12, replace "2" with --21--.

In column 7, Line 50, after "in" insert --the frame at--.

Signed and Sealed this

Fourth Day of October, 1994

Attest:

BRUCE LEHMAN

Attesting Officer　　Commissioner of Patents and Trademarks